(12) United States Patent
Tai et al.

(10) Patent No.: US 6,287,831 B1
(45) Date of Patent: Sep. 11, 2001

(54) CELL LYSIS DEVICE

(75) Inventors: Yu-Chong Tai, Pasadena; Sang-Wook Lee, Fullerton, both of CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 09/191,268

(22) Filed: Nov. 12, 1998

Related U.S. Application Data

(60) Provisional application No. 60/065,705, filed on Nov. 14, 1997.

(51) Int. Cl.$^7$ .............................. C12N 13/00; C12M 1/33; C12M 3/08
(52) U.S. Cl. ................................... 435/173.7; 435/173.1; 435/306.1; 204/194; 204/280; 204/600
(58) Field of Search ........................... 435/173.7, 173.1, 435/306.1; 204/194, 280, 600

(56) References Cited

U.S. PATENT DOCUMENTS

| | | |
|---|---|---|
| 4,778,769 | * 10/1988 | Forrest et al. . |
| 4,832,814 | 5/1989 | Root . |
| 4,971,910 | 11/1990 | Zimmermann . |
| 4,975,175 | * 12/1990 | Karube et al. . |
| 5,491,097 | * 2/1996 | Ribi et al. . |

OTHER PUBLICATIONS

Cheng et al. Nature Biotechnology vol. 16, pp. 541–546, Jun. 1998.

* cited by examiner

Primary Examiner—Christopher R. Tate
(74) Attorney, Agent, or Firm—Fish & Richardson P.C.

(57) ABSTRACT

A micromachined cell lysis device with electrodes that are spaced less than 100 µm from one another. The cells are attracted to the space between the electrodes and then lysed.

11 Claims, 4 Drawing Sheets

Oxidation

Cr-Au evaporation and pattern

Parylene C deposition and pattern

Packaging with glass channel

CELL LYSIS DEVICE

CROSS REFERENCE TO RELATED APPLICATIONS

This application claims the benefit of the U.S. Provisional Application No. 60/065,705, filed on Nov. 14, 1997, which is incorporated herein by reference.

STATEMENT AS TO FEDERALLY SPONSORED RESEARCH

The U.S. Government may have certain rights in this invention pursuant to Grant No. N66001-96-C-8632 awarded by the U.S. Navy.

BACKGROUND

It is known that an electrical field can be used to manipulate cells. Electrical manipulation of cells can be used for separating cells, holding cells, killing micro-organisms, or other operations.

Electrical manipulation of a cell is based on dielectrophoresis. A neutral particle, such as a microbial cell, will become polarized when subjected to a non-uniform electric field. Due to the non-uniformity of the field, a net force will act on the particle. This force will produce movement of the suspended cell. This phenomenon known as dielectrophoresis. the inside of the cell has and holds a different charge than the outside of the cell.

Macro sized electroporation systems have been designed for injecting genes into cells. See, "Electroporation and Electrofusion in Cell Biology," E. Newman, A. E. Sauer, C. A. Jordan, ed. Plenum Press, N.Y. 1989. These systems often use electrical fields to make microsized pores on cell membranes.

Cell lysis typically refers to opening a cell membrane to allow the cell interior to come out. Cell lysing can be used to obtain intracellular material for further analysis such as DNA identification.

It is known to use the science of micromachining to manipulate cells. See, for example, S. Lee, "A Study of Fabrication and Applications of Micromachined Cell Manipulating Devices," Ph.D. Thesis, Seoul National University, pp. 77–81, 1996. However, no one has previously reported using micromachining to form a device for cell lysis. Usually, these systems use cuvets that have a few millimeter range electrode gap. Lysing cells with this kind of size requires a few kilovolts of voltage source across such a gap.

Prior cell lysing has been reported using pulsed electric fields in a macrosized electroporation system. See, for example, T. Grahl and H. Markl, "Killing of Microorganisms by Pulsed Electric Fields," Appl. Microbio. Biotechnol., 45, pp. 148–157, 1996. The disadvantages of such a macrosized device have been described above.

J. Cheng, et al, "Preparation and Hybridization analysis of DNA/RNA from *E. Coli* on Microfabriacted Bioelectronic Chips" has suggested electronic cell lysis on a chip. However, this system still required hundreds of volts for lysing the cell.

SUMMARY

The present disclosure describes a new micromachined cell lysis device. A microsized cell lysis device as disclosed reduces the size of the entire system including the power source, since the electrode gap could be reduced to a few $\mu$m or smaller. This micro-sized cell lysis device is capable of operating on a small number of cells due to its small size.

A special way of using the electric field that can greatly simplify the purification steps is described. This can be used to prepare biosamples. In addition, the small size allows a reduction in voltage required for lysing. The voltage can be reduced to practical levels, e.g., less than 50 volts, since the electrode gap is on the order of microns.

A new structure is also described for cell lysis.

BRIEF DESCRIPTION OF THE DRAWING

These and other advantages will now be described in detail with respect to the accompanying drawings, wherein.

DESCRIPTION OF THE PREFERRED EMBODIMENTS

Figure 1A:
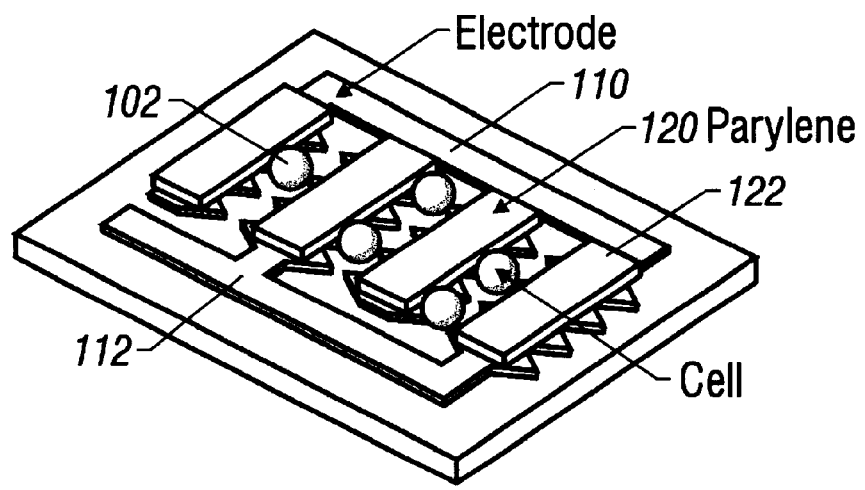
FIG. 1 shows a schematic view of the overall cell lysis device.
FIG. 1B shows a top view of the cell lysis electrode.
Figure 1B:
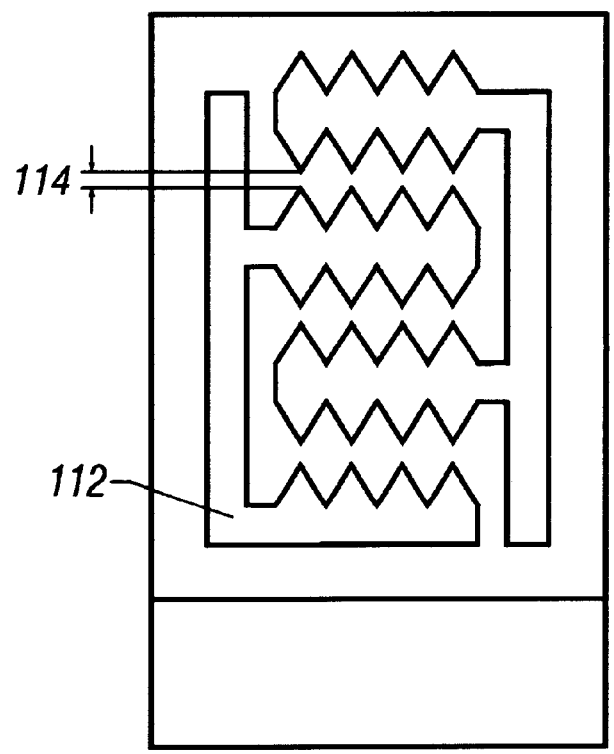

The basic lysis device is shown in plan view in FIGS. 1 and 1B. The device is made according to the fabrication steps explained below with reference to FIGS. 2A–2D.

The micromachining operates to form features on a silicon substrate.

Figure 2A:
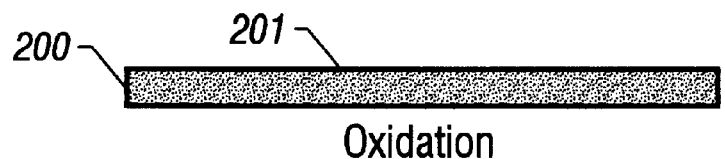
FIGS. 2A–2D show the fabrication steps of the cell lysis device.
Figure 2B:
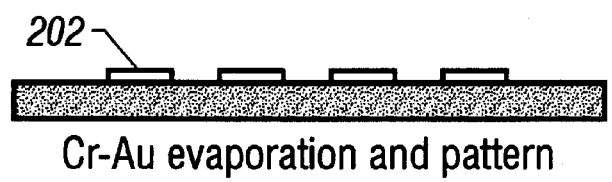

First an insulator is formed on the silicon substrate, by oxidizing the silicon substrate 200 to form a thermally-grown 5000 Å silicon oxide layer 201 as shown in FIG. 2A. Chromium/gold (Cr/Au) is thermally evaporated and patterned to form electrodes 202 on the oxidized surface. The electrodes are formed with a number of pointed portions facing one another, in the general shape shown in FIG. 1B.

Figure 2C:
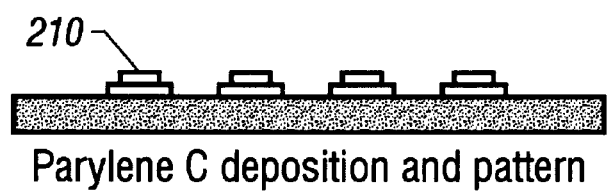

A 4 $\mu$m thick Parylene layer is deposited and patterned to form Parylene barriers 210 as shown in FIG. 2C. These barriers have side surfaces that hold the cell in a proper place, and form blocks between each pair of electrode surfaces.

Figure 2D:
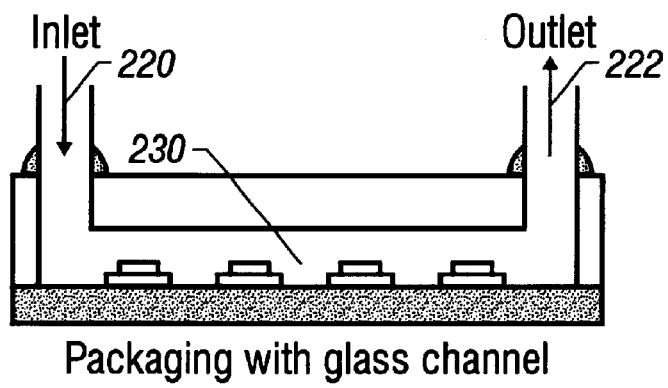

FIG. 2D shows bonding the thus-made assembly to a glass substrate which has an inlet 220, an outlet 222, and a channel 230 between the inlet and outlet. The channel is 30 $\mu$m high, made by timed wet etching.

The preferred device is designed for yeast cells. The distance between electrodes is hence around 5 $\mu$m. More generally, the distance can range between about 0.8 $\mu$m and 100 $\mu$m (0.1 mm), more preferably on the order of e.g. 1–9.9 $\mu$m.

The final assembled device is shown in FIG. 1. A number of cells are shown, such as cell 102. Cells are attracted by the dielectrophoretic force using an AC voltage. The cells are then lysed, using pulsed electric fields. The AC voltage depends on the conductivity and permitivity of the cell suspensions and the sizes of the cells. The cells are held between two electrodes 110, 112 and between the Parylene barriers 120, 122 for the lysing.

Any arrangement of pairs of electrodes, such as interdigitated or parallel, can be used for the cell lysing. Preferably, the edges of the electrodes are made sharp as shown in order to concentrate the field better on the cells. The nearest distance 114 between the two electrodes is preferably equal to the mean diameter of a cell plus the standard deviation of the cells in order to obtain the most effective lysing.

FIG. 1A shows a drawing of the electrode without the Parylene barriers present showing interdigitated electrodes. Distance 114 is defined as the distance between the sharp ends of the electrodes.

Figure 3:
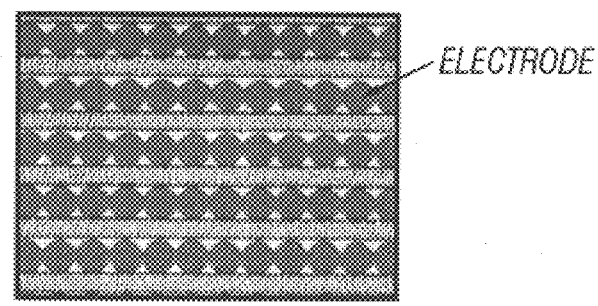
FIG. 3 shows a photograph of a fabricated device.
Figure 3:

FIG. 3 shows a drawing of the device from the top, showing all the arrangements of the various structures.

Figure 4:
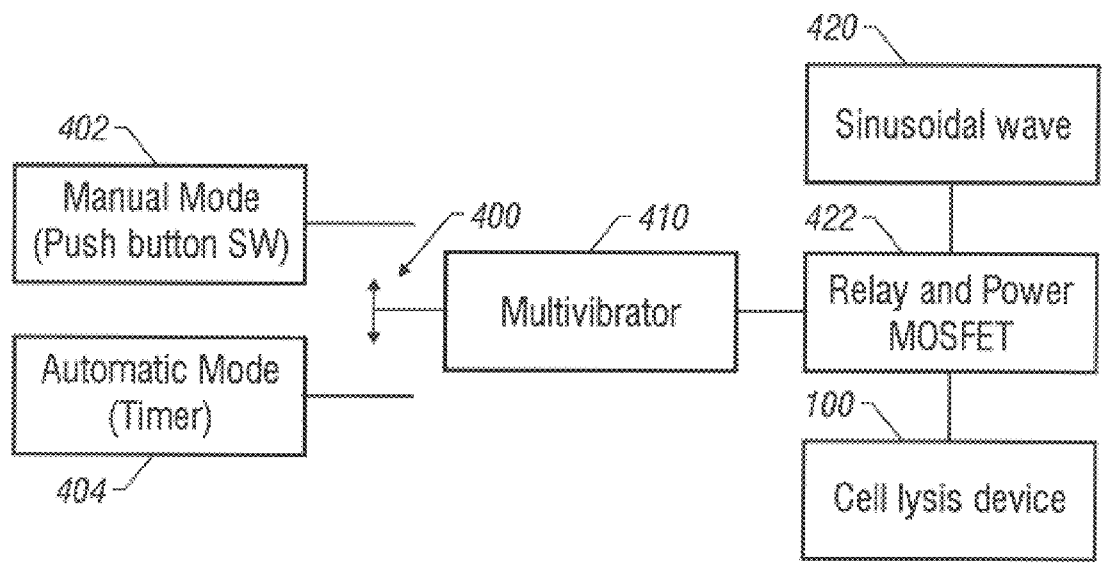
FIG. 4 shows schematically the power system used for cell lysis.

An important feature includes how the device is operated. A power system for the cell lysis is formed as shown in FIG. 4. Control is selected by a switch 400 which selects between manual mode or automatic mode. In the manual mode, the pulse is applied by a push-button switch 402. In the automatic mode, pulses are supplied at every defined interval. Pulse width control is provided by a multivibrator 410, typically a TTL-type multivibrator, part 74LS123. The switch 400 can be a single-pull, double-throw type relay.

A multipurpose function generator 420 provides the electric fields which attracts the cells. The electric field is preferably a sinusoidal wave. A power MOSFET 422 provides the output to the cell lysis device 100.

Figure 5:
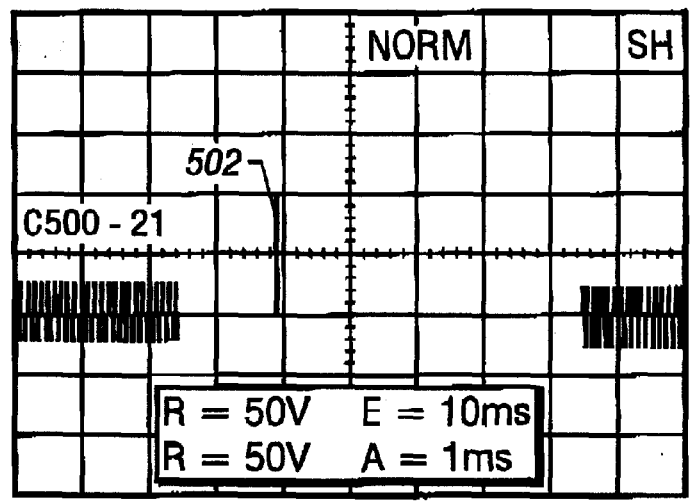
FIG. 5 shows a plot of a waveform for cell lysis.

A typical waveform is shown in FIG. 5, which shows a sample plot of the waveform for cell lysis. The waveform includes two parts—the attraction phase 500, and the lysing phase 502.

The attraction phase uses a 6 volt AC, 2 MHZ sample. This attracts the cells to the lysing locations. A sinusoidal wave is preferably used to attract the cell to the location. After a short delay, lysing pulse, a 100 $\mu$s, 20 volt pulse, is applied.

Figure 6:
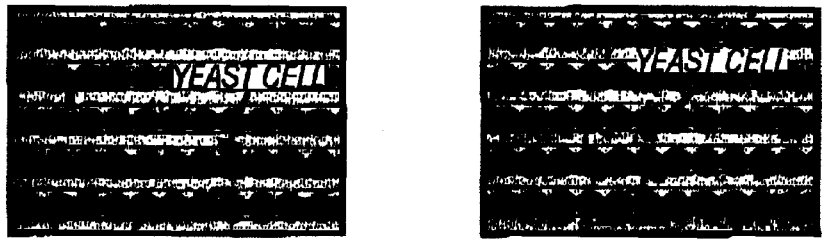
FIG. 6 shows drawings of yeast cells before and after lysing.

FIGS. 6A and 6B show the yeast cells before and after applying the pulsed voltage. FIG. 6A shows attraction of the yeast cells to the electrode when the 2 MHZ 6V AC voltage in FIG. 5 is applied. FIG. 6B shows the result of lysing. After lysing the cells, the inside and outside of the cells are electrically connected, and they will no longer attract to the electrodes by the AC voltage.

Figure 7:
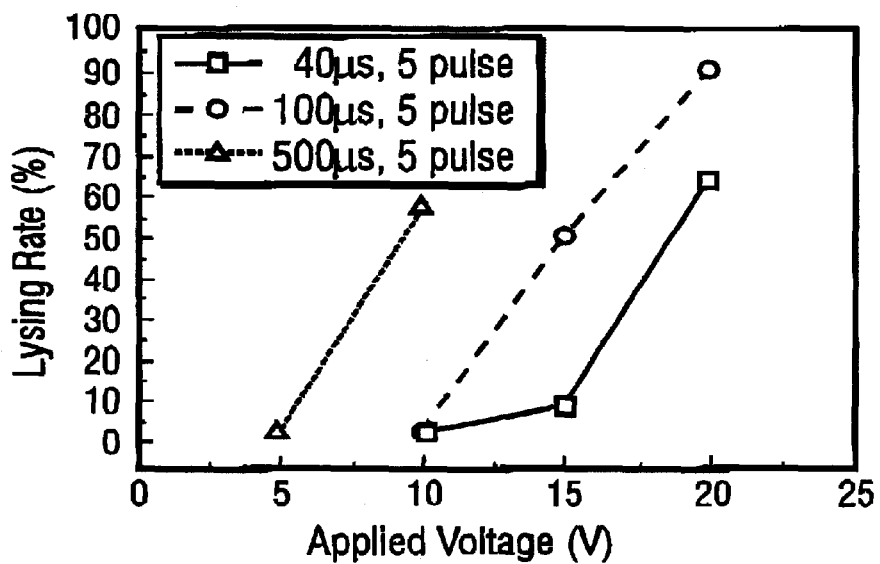
FIG. 7 shows a plot of lysis vs voltage.

FIG. 7 shows some representative lysing rates with different electric fields and pulse durations. The rate is increased with increased voltage and duration. Excessive pulse voltage and duration form electrolysis effects. The optimum value for yeast cell lysing is believed to occur at 100 $\mu$s and 20V. However, any voltage less than 50 volts is preferred and within the preferred embodiment.

Although only a few embodiments have been described in detail above, other embodiments are contemplated by the inventor and are intended to be encompassed within the following claims. In addition, other modifications are contemplated and are also intended to be covered. For example, other shapes and sizes of electrodes could be used. There could also be more than two electrodes. While the pointed electrodes are preferred, flat shaped electrodes can also be used.

What is claimed is:

1. A micromachined cell lysis device, comprising:
   a silicon substrate;
   an insulator, covering at least a portion of said silicon substrate;
   at least two electrodes, formed on said insulator, and between which an applied electric field can be provided;
   a distance between said electrodes being less than 100 $\mu$m; and
   wherein said electrodes have sharp edges facing each other, and a distance between said sharp edges is less than 100 $\mu$m.

2. A device as in claim 1 further comprising at least two cell blocker elements, providing physical barriers which extend to hold a cell into place at a desired location between said sharp edges of said two electrodes.

3. A device as in claim 2, wherein said cell blocker elements are formed of Parylene.

4. A micromachined cell lysis device, comprising:
   a silicon substrate;
   an insulator, covering at least a portion of said silicon substrate;
   at least two electrodes, having sharp edges which face one another formed on said insulator, and between which an applied electric field can be provided;
   wherein said distance is less than 10 $\mu$m;
   wherein a distance between the sharp edges of said at least two electrodes is substantially a mean diameter of a desired cell plus a standard deviation among cells.

5. A method of forming a cell lysis device using micromachining techniques, comprising:
   obtaining a substrate;
   forming two electrode patterns on the substrate, each of which have sharp edges facing one another with a distance between said two desired electrode patterns of less than 100 $\mu$m;
   forming blocks for the cells to hold the cells at a location between said electrodes.

6. A method as in claim 5, wherein said distance is less than 10 $\mu$m.

7. A method as in claim 5, wherein a distance between sharp points of said two electrodes is substantially a mean diameter of a desired cell plus a standard deviation among cells.

8. A method as in claim 6, wherein said cell blocker elements are formed of Parylene.

9. A method of forming a cell lysis device using micromachining techniques and lysing a cell using the cell lysis device, comprising:
   obtaining a substrate;
   forming two desired electrode patterns on the substrate each of which have sharp edges facing one another, with a distance between said two desired electrode patterns of less than 100 $\mu$m;
   forming blocks for the cells to hold the cells at a location between said electrodes;
   applying an AC voltage less than 50 volts peak to peak between said electrodes to attract a cell using dielectrophoretic force to a spot between said electrodes; and
   then, after said cell is attracted, applying a spike of DC voltage, to lyse said cell.

10. A method of lysing a cell, comprising:
    obtaining a cell lysis device on a silicon substrate which includes two desired electrode patterns on the substrate, each of said electrode pattern having at least one sharp portion, said sharp portions facing one another, with a distance between said two desired electrode patterns of less than 100 $\mu$m; and
    applying a first AC lower voltage between said electrodes to attract a cell to a spot between said electrodes dielectrophoretic; and
    then, after said cell is attracted, applying a spike of DC higher voltage, to lyse said cell, wherein each of said voltages is less than 50 volts.

11. A method as in claim 10, wherein each of said voltages is less than or equal to 20 volts.

\* \* \* \* \*